United States Patent [19]

Smith, III

[11] Patent Number: 4,832,687
[45] Date of Patent: May 23, 1989

[54] SUBCUTANEOUS TUNNELING INSTRUMENT AND METHOD

[76] Inventor: Ray C. Smith, III, 7544 Iron Horse La., Indianapolis, Ind. 46256

[21] Appl. No.: 140,120

[22] Filed: Dec. 31, 1987

[51] Int. Cl.$^4$ ............................................. A61M 25/00
[52] U.S. Cl. ....................................... 604/51; 604/274
[58] Field of Search ...................................... 604/51–53, 604/164, 264, 272–274, 280; 128/348.1

[56] References Cited

U.S. PATENT DOCUMENTS

| | | | |
|---|---|---|---|
| 3,861,393 | 1/1975 | Durand | 604/274 |
| 4,299,228 | 11/1981 | Peters | 604/53 X |
| 4,327,722 | 5/1982 | Groshong et al. | 604/53 |
| 4,432,752 | 2/1984 | Marlon | |
| 4,453,928 | 6/1984 | Steiger | 604/53 |
| 4,699,612 | 10/1987 | Hamacher | 604/274 |

OTHER PUBLICATIONS

"Technique for Placement of a Permanent Home Hyperalimentation Catheter," by David M. Heimbach, M.D. and Tom D. Ivey, M.D., *Surgery Gynecology & Obstetrics*, Oct. 1976, vol. 143, pp. 635–636.

*Primary Examiner*—Dalton L. Truluck
*Attorney, Agent, or Firm*—Woodward, Emhardt, Naughton, Moriarty & McNett

[57] ABSTRACT

A novel subcutaneous tunnelling instrument and method for placing a subcutaneous catheter between two remote incisions in a patient, comprising making a subcutaneous tunnel by pushing a rod having an elongated bullet-shaped tip removably threaded upon male threads disposed at the distal end thereof into one incision and subcutaneously tunnelling to and out through the second incision, removing the bullet-shaped tip from the distal end of the rod, sliding the open end of a catheter over the male threads disposed at the distal end of the rod until the catheter abuts the rod, thereafter pulling the distal end of the rod back into the second incision and through the subcutaneous tunnel to and through the first incision, and thereafter removing the open end of the catheter from the male threads at the distal end of the rod.

12 Claims, 2 Drawing Sheets

SUBCUTANEOUS TUNNELING INSTRUMENT AND METHOD

BACKGROUND OF THE INVENTION

The present invention relates to the fields of apparatus and methods for the subcutaneous placement of catheters, and more particularly to a novel subcutaneous tunneling instrument and method of utilizing the same.

The desirability and methods of utilizing small subcutaneous permanent home hyperalimentation catheters of the Hickman or Broviac type are known in the art and are discussed in various journal articles. An exemplary technique for using a Broviac type catheter is described in an article entitled "Technique for Placement of a Permanent Home Hyperalimentation Catheter," by David M. Heimbach, M.D., and Tom D. Ivey, M.D., *Surgery, Gynecology & Obstetrics*, October 1976, Volume 143, pp. 635-36, which is incorporated herein by reference. An exemplary technique for using a Hickman type catheter is described in U.S. Pat. No. 4,432,752, "Procedure for Introducing Hyperalimentation Catheters and the Like," issued to Marlon on Feb. 24, 1984, which is also incorporated herein by reference.

Also known are the desirability and methods of utilizing long subcutaneous catheters in neurosurgery, ventricular, and peritoneal shunts, which are also discussed in various journal articles.

Known methods of placing subcutaneous permanent home hyperalimentation catheters involve the forcible, trauma inducing formation of a subcutaneous catheter tunnel through which the desired catheter is to be led. In the prior art, subcutaneous tunnels have been formed by means of forcing blunt, trauma inducing tunneling instruments along the selected subcutaneous path or by utilizing instruments having sharp blades at their proximate ends that literally and indiscriminately cut through subcutaneous tissue, both fatty tissue and blood vessels alike. Examples of tunnelling instruments of the former category are the vaginal packing forceps disclosed in the Heimbach article cited above, or the somewhat less traumatic blunt-nosed rigid tunneling catheter disclosed in U.S. Pat. No. 4,432,752 to Marlon.

Another known tunnelling instrument is a stainless steel trocar, which is a sharp-pointed instrument fitted within the lumen of a reusable cannula sheath, which is forced along the desired subcutaneous path to create the subcutaneous tunnel. However, not only does the sharp point of the instrument undesirably cut subcutaneous tissue as it is tunnelled though tissue, but the forward edges of the cannula sheath also tear at subcutaneous tissue as the trocar is forced along its path. Once the desired subcutaneous tunnelling has been completed, the stainless steal instrument is removed from the lumen of the cannula sheath, which remains in place, and the catheter of choice is fed through the lumen of the cannula sheath. The cannular sheath is then removed from the subcutaneous tunnel by slipping the cannula sheath off of the indwelling catheter. A device of this type is known in the art as the Steiger Tunneling Instrument, which is available commercially through Evermed of Kirkland, Washington.

The novel tunnelling instrument of the present invention provides for less traumatic placements of permanent home hyperalimentation catheters and shunts than has heretofore been known in the prior art.

SUMMARY OF THE INVENTION

One embodiment of the present invention is a subcutaneous tunnelling instrument for placing a subcutaneous catheter, comprising a bendable rod of circular cross section, having a diameter equal to the outer diameter of the catheter, male threads at the distal end portion of the rod, having a height between corresponding thread points equal to about the inner diameter of the catheter, and an elongated bullet-shaped tip removably threadable upon the male threads.

Another embodiment of the present invention is a method for the placement of a subcutaneous catheter between two remote incisions in a patient, comprising the steps of (a) making a subcutaneous tunnel by pushing a bendable rod having an elongated bullet-shaped tip removably threaded upon male threads disposed at the distal end of the rod into one incision and subcutaneously to and out through the second incision, (b) removing the bullet-shaped tip from the distal end of the rod, (c) sliding the open end of a catheter over the male threads disposed at the distal end of the rod until the catheter abuts the rod, (d) after step c., pulling the distal end of the rod back into the second incision and through the subcutaneous tunnel to and through the first incision, and (e) after step d., removing the open end of the catheter from the male threads.

It is an object of the present invention to provide a subcutaneous tunneling instrument that provides for less traumatic placement of subcutaneous catheters in patients.

It is a further object of the present invention to provide a a less traumatic method for the subcutaneous placement of catheters in patients.

Further objects and advantages of the present invention will be evident from the following description of the drawings and the preferred embodiments.

DESCRIPTION OF THE PREFERRED EMBODIMENT

Figure 1:
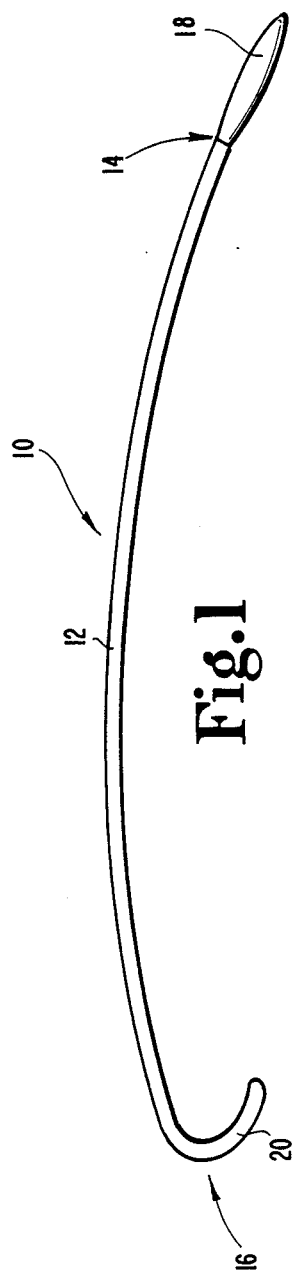
FIG. 1 is a plan view of the preferred embodiment of the subcutaneous tunneling instrument of the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now to the drawings, there is shown in FIG. 1 a plan view of the preferred embodiment of the subcutaneous tunneling instrument of the present invention 10. In the preferred embodiment, tunneling instrument 10 is comprised of a rod 12 of circular cross section of a constant diameter, having a distal end portion 14 and a proximate end portion 16. The length of rod 12 from the proximate end portion 16 to the distal end portion 14 will be determined by the length of the desired subcutaneous tunnel.

In FIG. 1, rod 12 is shown with a slight curvature along its length. It is preferred that rod 12 be constructed from a material that is both suitably rigid to permit forcible subcutaneous tunneling without wandering from the desired subcutaneous path, yet be pliable enough to permit the surgeon to pre-shape shape rod 12 prior to subcutaneous insertion to approximate to be subcutaneous tunnel path to be fashioned therewith. Of course, the material chosen must also be selected so as to be suitable for surgical procedures, such as autoclave sterilization. In the preferred embodiment, surgical grade stainless steel has been chosen, as it readily meets both of the these foregoing criteria, but other suitable materials may be utilized, and the present invention is not to be interpreted as limited to the use of stainless steel materials.

At the proximate end portion 16 of the preferred embodiment (FIG. 1), rod 12 has a further bent portion 20, which provides the surgeon with a convenient hand or finger hold upon rod 20 at its proximate end suitable for use during tunnelling. At the distal end portion 14 of the preferred embodiment (FIGS. 1 and 2), rod 12 is provided with a removable, elongated bullet-shaped tip 18, having a maximum diameter "a" (FIG. 2) slightly larger than diameter "b" (FIG. 2) of rod 12. In the preferred embodiment, tip 18 is removably secured to the distal end portion of rod 20 by conventional treaded engagement, with tip 18 providing the female threads 22 and rod 12 the male threads 24 to provide such treaded engagement.

Figure 3:
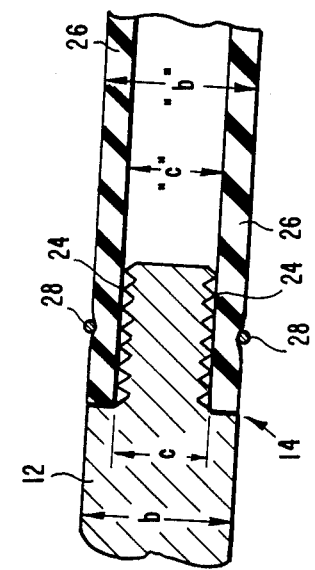
FIG. 3 is an enlarged segmented plan view of the distal end of the subcutaneous tunneling instrument as configured in of FIG. 4.
Figure 2:
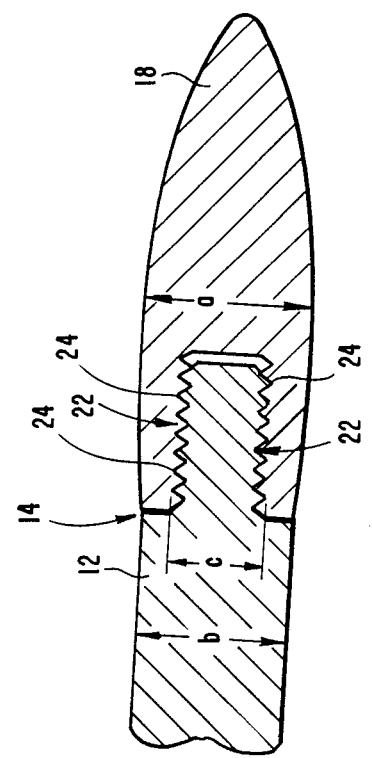
FIG. 2 is an enlarged segmented view of the distal tip portion of the instrument of FIG. 1.

Referring to FIGS. 2 and 3, in the preferred embodiment, male threads 24 are sized to be a height "c" between corresponding thread points such that male threads 24 snuggly receive a subcutaneous catheter 26 (FIG. 3) having an inner diameter of "c" and an outer diameter of "b" corresponding to the diameter "b" of rod 12. As a result of this corresponding relationship, catheter 26 and rod 12 will abut at distal end portion 14 of rod 12 each having diameter "b," and there will therefore no ridges created by rod 12 or catheter 26 about proximate end portion 14 of rod 12. Referring to FIG. 3, catheter 26 can be secured in place as shown with a simple surgical stitch 28 about the catheter 26 and over male threads 24. As can be discerned from the foregoing discussion, rod 12 and male thread 24 can be varyingly sized to receive catheters 26 of varying internal diameters "c" and outer diameters "b," allowing the tunneling instrument of the present invention to be provided in multiple sizes to accommodate the specific size requirements of the catheter to be placed.

Figure 6:
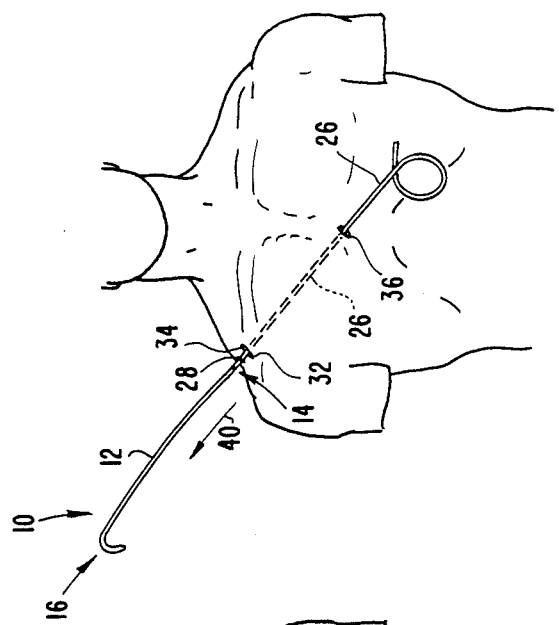
FIG. 6 is a diagramatic view of the patient demonstrating the subcutaneous placement the desired catheter in accordance with the present invention.
Figure 5:
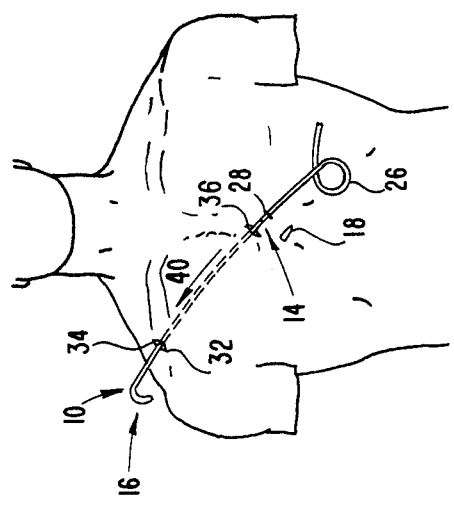
FIG. 5 is a diagramatic view of the patient of FIG. 3 demonstrating the subcutaneous tunneling instrument of FIG. 1 with the distal tip portion removed and the catheter to be subcutaneously placed secured by a stitch to the distal end thereof in accordanc with the present invention.
Figure 4:
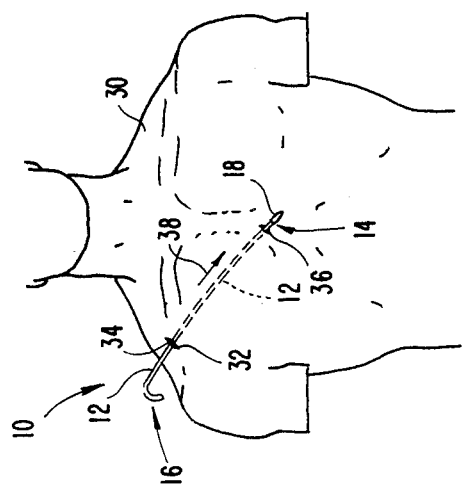
FIG. 4 is a diagramatic view of a patient demonstrating the incisions and the subcutaneous tunneling instrument of FIG. 1 through the respective incisions and subcutaneously placed in preparation for the placement of a Hickman or Broviac type catheter in accordance with the present invention.

Referring now to FIGS. 4–6, there is shown, in diagramatic views of patient 30, the subcutaneous tunneling instrument 10 of the present invention utilized in one example of the novel method of placement of a permanent home hyperalimentation Hickman- or Broviac-type catheter in accordance with the present invention. Referring to FIG. 4, incision 32 is made to isolate the cephalic vein 34 (not shown) and the deltopectoral groove is disected at incision 36. Tunnelling instrument 10 of the present invention, with bullet tip 18 attached, is then subcutaneously tunnelled from entering incision 32 to exiting incision 36 in the direction of arrow 38 (FIG. 4). Bullet tip 18 with its rounded tip has been demonstrated to date to push through subcutaneous tissue less traumatically than tunnellers of the prior art. The slightly larger maximum diameter of bullet tip 18 over that of rod 12 desirably provides a subcutaneous tunnel slightly larger that required to snuggly accommodate rod 12.

Referring now to FIGS. 4 and 5, when bullet tip 18 exits the subcutaneous tunnel through incision 36, bullet tip 18 is removed from the distal end 14 of rod 12 (FIG. 5) and catheter 26 is placed over male threads 24 in the manner described above until catheter 26 abuts the proximate end 14 of rod 12 as shown in FIG. 3. Catheter 26 is secured to rod 12 by a single stitch 28, as previously described. Rod 12 is then withdrawn from the subcutaneous tunnel in the direction of arrow 40 in FIG. 5, pulling catheter 26 through the subcutaneous tunnel immediately behind exiting rod 12 until the proximate end 14 of rod 12 exits entering incision 32. Suter ligature 28 may then be removed from catheter 26 and catheter 26 may be removed from its engagement with male threads 24 of rod 12, allowing catheter 26 to then be located within the isolated cephalic vein 34 and otherwise permanently located by known and conventional means.

While the inventions have been illustrated and described in detail in the drawings and foregoing description, the same is to be considered as illustrative and not restrictive in character, it being understood that only the preferred embodiment of the tunnelling instrument of the present invention has been shown and described and that only one example of the novel tunnelling process of the present invention has been described and illustrated and that all changes and modifications of the tunnelling instrument of the present invention and applications of the novel process of the present invention that come within the spirit of the invention are desired to be protected.

What is claimed is:

1. A subcutaneous tunnelling instrument for placing a subcutaneous catheter, comprising:
   a bendable rod of circular cross section, having a diameter equal to about the outer diameter of the catheter;
   male threads at the distal end portion of said rod, having a height between corresponding thread points equal to about the inner diameter of the catheter; and
   an elongated bullet-shaped tip removably threadable upon said male threads.

2. The subcutaneous tunnelling instrument of claim 1 wherein said bullet-shaped tip abuts said rod in flush relationship when fully threaded upon said male threads, said rod and said tip being of equal cross sectional area and diameter where abutted.

3. The subcutaneous tunnelling instrument of claim 1 wherein said bullet-shaped top has a maximum cross sectional diameter greater than the diameter of said rod.

4. The subcutaneous tunnelling instrument of claim 1 wherein said rod is stainless steel.

5. A method for the placement of a subcutaneous catheter between the two remote incisions in a patient, comprising the steps of:
 a. making a subcutaneous tunnel by pushing a bendable rod having an elongated bullet-shaped tip removably threaded upon mail threads disposed at the distal end thereof into one incision and subcutaneously to and out through the second incision;
 b. removing the bullet-shaped tip from the distal end of the rod;
 c. sliding the open end of a catheter over the male threads disposed at the distal end of the rod until the catheter abuts the rod;
 d. after step c., pulling the distal end of the rod back into the second incision and through the subcutaneous tunnel to and through the first incision; and
 e. after step d., removing the open end of the catheter from the male threads.

6. The method of claim 5 wherein step a. includes a rod of circular cross section with a diameter equal to about the outer diameter of the catheter.

7. The method of claim 6 wherein step a. includes male threads having a height between corresponding thread points equal to about the inner diameter of the catheter.

8. The method of claim 7 wherein step a. includes an elongated bullet-shaped tip.

9. The method of claim 8 wherein step a. includes an elongated bullet-shaped tip having a maximum cross-sectional diameter that is greater than the cross sectional diameter of the rod.

10. The method of claim 8 wherein step a. includes an elongated bullet-shaped tip that abuts the rod in flush relationship when fully threaded upon the male threads, the rod and bullet-shaped tip being of equal cross sectional area and diameter where abutted.

11. The method of claim 5 wherein step a. comprises the substeps of receiving an open end of the catheter over the male threads until the catheter abuts rod 12 in flush relationship and thereafter securing the catheter in place with at least one suter ligature place about the circumference of the catheter.

12. The method of claim 11 wherein step a. includes a stainless steel rod.

* * * * *

UNITED STATES PATENT AND TRADEMARK OFFICE
CERTIFICATE OF CORRECTION.

PATENT NO. : 4,832,687

DATED : May 23, 1989

INVENTOR(S) : Ray C. Smith, III

It is certified that error appears in the above-identified patent and that said Letters Patent is hereby corrected as shown below:

In column 2, line 64, delete the word "accordanc" and place in lieu thereof the word --accordance--.

In column 6, line 25, delete the word "place" at its second occurrence and place in lieu thereof the word --placed--.

Signed and Sealed this

Sixteenth Day of January, 1990

*Attest:*

JEFFREY M. SAMUELS

*Attesting Officer*    *Acting Commissioner of Patents and Trademarks*